US00PP36790P2

(12) United States Plant Patent
Miller

(10) Patent No.: US PP36,790 P2
(45) Date of Patent: Jul. 1, 2025

(54) ***CATHARANTHUS* PLANT NAMED 'CARZ0002'**

(50) Latin Name: *Catharathus roseus*
Varietal Denomination: CARZ0002

(71) Applicant: SYNGENTA CROP PROTECTION AG, Basel (CH)

(72) Inventor: Baylee Miller, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 18/831,320

(22) Filed: Nov. 12, 2024

(51) Int. Cl.
*A01H 5/02* (2018.01)
*A01H 6/08* (2018.01)

(52) U.S. Cl.
USPC ..... Plt./263.1
CPC ..... *A01H 6/084* (2018.05)

(58) Field of Classification Search
USPC ..... Plt./263.1
CPC ..... A01H 5/02
See application file for complete search history.

*Primary Examiner* — Kent L Bell
(74) *Attorney, Agent, or Firm* — Dale Skalla

(57) ABSTRACT

'CARZ0002' is a product of a planned breeding program. The new cultivar 'CARZ0002' has medium sized cranberry and white bi-colored flowers, excellent flower production, moderate plant size and uniform mounding and somewhat spreading habit with medium green foliage.

1 Drawing Sheet

Latin name of the genus and species of the plant claimed: *Catharathus roseus.*

DETAILED DESCRIPTION

*Catharanthus* variety 'CARZ0002' disclosed in the present application has shown uniformity and stability, as described in the following section. *Catharanthus* variety 'CARZ0002' disclosed in the present application has been asexually reproduced a sufficient number of generations with careful attention to uniformity of plant type and has been increased with continued observation for uniformity.

Origin of 'CARZ0002'

'CARZ0002' is a product of a planned breeding program. The new cultivar 'CARZ0002' has medium sized cranberry and white bi-colored flowers, excellent flower production, moderate plant size and uniform mounding and somewhat spreading habit with medium green foliage.

'CARZ0002'originates from a planned self-pollination in an indoor greenhouse in August 2015 in Gilroy, California. The parent was identified as 'FF 1835-1', having medium flowers of rose and white bi-color and upright habit compared to 'CARZ0002'.

The seed was sown in March 2016 in a greenhouse in Gilroy, California. 'CARZ0002' was selected as a single flowering plant within the progeny of the stated self-pollination in March 2017.

The first act of asexual reproduction of 'CARZ0002' was accomplished when vegetative cuttings were propagated from the initial selection in January 2019 in a greenhouse in Gilroy, California.

Horticultural examination of plants grown from cuttings of the original plant in January 2019, in Gilroy, California, and continuing thereafter, has demonstrated that the combination of characteristics as herein disclosed for 'CARZ0002' are firmly fixed and are retained through successive generations of asexual reproduction.

'CARZ0002' has not been observed under all possible environmental conditions. The phenotype may vary significantly with variations in environment such as temperature, light intensity, disease exposure, and day length.

TABLE 1

DIFFERENCES BETWEEN THE NEW VARIETY 'CARZ0002' AND A MOST SIMILAR VARIETY

| | 'CARZ0002' | 'Titan Cranberry', Protected under U.S. Pat. No. 10,212,908 |
|---|---|---|
| Flower color: | Cranberry color on outer edge of petals with white color on inner part of petals with a white eye | Cranberry colored petals with very small white eye |
| Disease resistance: | Known disease resistance to *Phytophthora nicotianae* | No known disease resistance to *Phytophthora nicotianae* |
| Plant habit: | Mounded and somewhat spreading | Mounded and compact |

Figure 1:
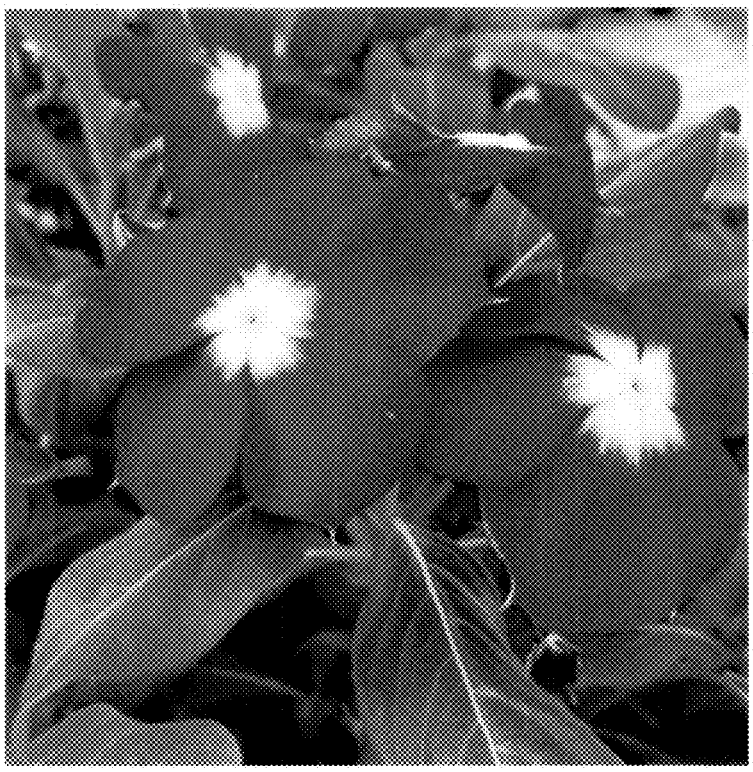
FIG. 1 shows a close view of an inflorescence. Taken on Jan. 3, 2023 in Gilroy, CA.
Figure 2:
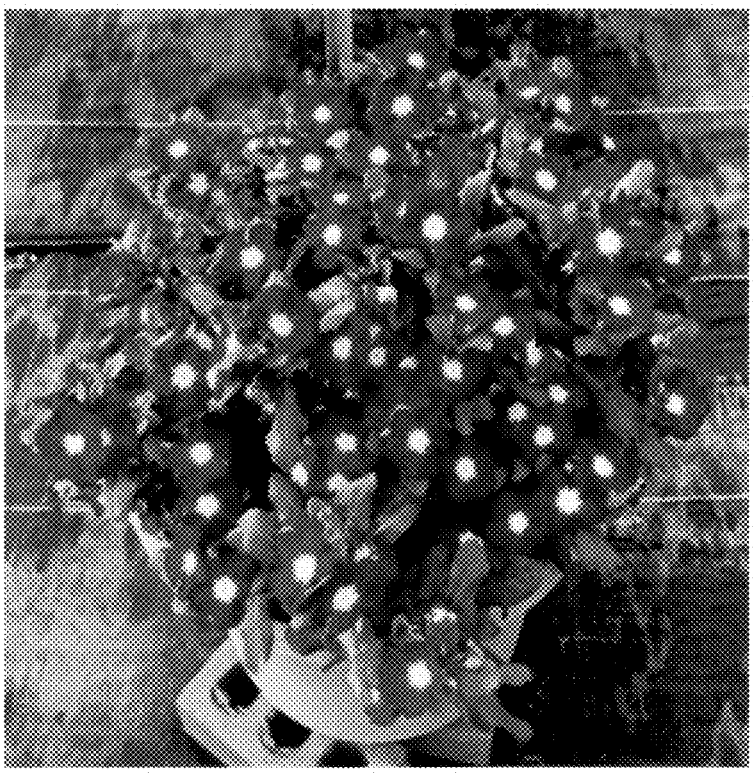
FIG. 2 shows a whole flowering plant. Taken on Jul. 25, 2022 in Monroeville, NJ.

The plant descriptions and measurements were taken in Gilroy, California in April 2024. The plants were approximately 14 weeks old and were growing in 4.5" pots in a greenhouse. The color descriptions provided are in reference to The R.H.S. Colour Chart, Sixth Edition (2015).

Plant:

*Form, growth and habit.*—Semi-woody, grown as an annual; mounding and somewhat spreading habit; very well branched.
*Plant height.*—24 cm.
*Plant height (inflorescence included).*—25 cm.
*Plant width.*—30 cm.
*USDA hardiness.*—10-11.

Roots:
*Description.*—Fibrous, freely branching.
*Habit.*—Taproot with smaller, branching lateral roots.
*Color.*—Closest to RHS NN 155C.

Foliage:
*Type.*—Opposite.
*Immature, leaf color, upper surface.*—Closest to RHS 144A.
*Lower surface.*—Closest to RHS 146B.
*Mature, leaf color, upper surface.*—Closest to RHS 141A.
*Lower surface.*—Closest to RHS 143A.
*Vein color, upper surface.*—Closest to RHS 145A.
*Vein color, lower surface.*—Closest to RHS 145D.
*Length.*—10.0-13.0 cm.
*Width.*—2.5-4.5 cm.
*Shape.*—Ovate.
*Base shape.*—Acute.
*Apex shape.*—Acuminate.
*Margin.*—Entire.
*Texture, upper surface.*—Smooth.
*Texture, lower surface.*—Smooth.
*Pattern of veining.*—Pinnate.
*Petioles color.*—Closest to RHS 142B.
*Petioles length.*—0.4-1.4 cm.
*Diameter of petiole.*—20 cm.
*Texture (upper and lower surface).*—Smooth.

Stem:
*Color of stem.*—Closest to RHS 142B.
*Length of stem.*—20-25 cm.
*Diameter.*—0.4-0.6 cm.
*Length of internodes.*—3.0-6.5 cm.
*Texture.*—Smooth.

Inflorescence:
*Type.*—Panicle.
*Blooming habit.*—Flowers continuously from spring through fall.
*Number of open flowers per inflorescence.*—About 2-6.
*Quantity of inflorescences per plant.*—About 24-36.
*Lastingness of individual blooms on the plant.*—About 2 weeks (depending on temperatures).
*Fragrance.*—Rose.

Flower:
*Arrangement.*—Arising from upper leaf axils, freely flowering, facing upwards and outwards.
*Floret form.*—Single salverform, tube with disc of petals.
*Length of floret.*—6.1 cm.
*Width of floret.*—6.1 cm.
*Depth of floret.*—2.8 cm.
*Peduncle length.*—0.3 cm.
*Peduncle diameter.*—0.2 cm.
*Peduncle texture.*—Smooth.
*Peduncle color.*—RHS 141C.
*Petal arrangement.*—Overlapping.
*Petal number.*—5.
*Petal shape.*—Obovate.
*Petal length.*—2.9 cm.
*Petal width.*—3.0-3.6 cm.
*Petal eye zone diameter.*—0.6-1.2 cm.
*Young floret, color upper surface.*—RHS 61B and RHS NN 155D.
*Young floret, color lower surface.*—RHS 72A and RHS 69D.
*Mature florets, color upper surface.*—RHS 61B and RHS NN 155D.
*Mature floret, color lower surface.*—RHS 72A and RHS 69D.
*Apex shape.*—Cuspidate.
*Degree of lobation.*—Deep.
*Margin.*—Crenate.
*Base.*—Fused.
*Texture, upper surface.*—Smooth.
*Lower surface.*—Smooth.
*Tube, color outer surface.*—Closest to RHS 184A and RHS 145B.
*Tube, color inner surface.*—Closest to RHS 184A and RHS 145B.
*Tube, length.*—2.5-3.0 cm.
*Tube, diameter (at opening).*—0.20 cm.
*Tube, texture outer surface.*—Smooth.
*Inner surface.*—Smooth.
*Bract number per flower.*—0.
*Sepal number per flower.*—5.
*Sepal shape.*—Lanceolate.
*Sepal margin.*—Smooth.

Bud (just before opening):
*Color.*—RHS 77B and RHS 145D.
*Length.*—1.8 cm.
*Width.*—0.6 cm at the widest point.
*Shape.*—Tubular.

Bract:
*Color.*—Closest to RHS 184A and RHS 145A.
*Length.*—0.7-1.1 cm.
*Diameter.*—0.15-0.2 cm.
*Texture, upper surface.*—Hirsute.
*Lower surface.*—Hirsute.

Calyx:
*Number of sepals.*—5, fused sepals forming a short tube around the base of the floret.
*Color of sepals.*—RHS 145A.
*Length of sepals.*—0.2-0.3 cm.
*Width of sepals.*—0.1 cm.
*Apex shape.*—Obtuse.
*Apex margins.*—Entire.
*Texture, outer surface.*—Pubescent.
*Inner surface.*—Glabrous.

Reproductive organs:
Gynoecium
*Pistil quantity.*—One.
*Length.*—0.35 cm.
*Style color.*—RHS 159D.
*Style length.*—0.2 cm.
*Stigma color.*—RHS 144B.
*Ovary color.*—RHS 144A.
*Ovary length.*—0.1 cm.
*Ovary diameter.*—0.05 cm.

Androecium
*Stamen quantity.*—4.
*Color of filaments.*—RHS 159D.
*Length filaments.*—0.05 cm.
*Anther color.*—RHS 164A.
*Length of anthers.*—0.1 cm.

*Color of pollen*.—RHS 10D.
*Pollen amount*.—Normal.
*Fertility/seed set*.—Male and female fertile, moderate seed set.
*Typical seed number*.—10-20.
*Seed length*.—0.3 cm.
*Seed width*.—0.1-0.2 cm.
*Seed color*.—RHS 203A.
*Disease/pest resistance*.—Exhibits strong resistance to aerial phytophthora (*Phytophthora nicotianae*); insect pest resistance not observed.

What is claimed is:

1. A new and distinct cultivar of *Catharanthus* plant named 'CARZ0002', substantially as illustrated and described herein.

* * * * *